(12) United States Patent
Corpa De La Fuente et al.

(10) Patent No.: US 12,070,233 B2
(45) Date of Patent: *Aug. 27, 2024

(54) FEATURE-BASED SURGICAL TOOL IDENTIFICATION

(71) Applicant: Smith & Nephew, Inc., Memphis, TN (US)

(72) Inventors: Cedric Corpa De La Fuente, Gibsonia, PA (US); Brett Bell, Mendon, UT (US)

(73) Assignee: Smith & Nephew, Inc., Memphis, TN (US)

( * ) Notice: Subject to any disclaimer, the term of this patent is extended or adjusted under 35 U.S.C. 154(b) by 280 days.

This patent is subject to a terminal disclaimer.

(21) Appl. No.: 17/551,485

(22) Filed: Dec. 15, 2021

(65) Prior Publication Data
US 2022/0104833 A1 Apr. 7, 2022

Related U.S. Application Data

(63) Continuation of application No. 16/521,796, filed on Jul. 25, 2019, now Pat. No. 11,207,079, which is a continuation of application No. 16/473,974, filed as application No. PCT/US2018/015316 on Jan. 25, 2018, now Pat. No. 10,575,860.

(60) Provisional application No. 62/450,458, filed on Jan. 25, 2017.

(51) Int. Cl.
*A61B 17/16* (2006.01)
*A61B 34/00* (2016.01)
*A61B 90/90* (2016.01)
*A61B 17/00* (2006.01)

(52) U.S. Cl.
CPC ...... *A61B 17/1615* (2013.01); *A61B 17/1617* (2013.01); *A61B 17/1626* (2013.01); *A61B 34/25* (2016.02); *A61B 90/90* (2016.02); *A61B 2017/00464* (2013.01); *A61B 2034/256* (2016.02)

(58) Field of Classification Search
CPC ............ A61B 17/1617; A61B 17/1626; A61B 17/1615
See application file for complete search history.

(56) References Cited

U.S. PATENT DOCUMENTS

| 2004/0220602 | A1* | 11/2004 | Deng | A61B 90/98 606/167 |
| 2013/0060278 | A1* | 3/2013 | Bozung | A61B 17/1675 606/205 |
| 2016/0135820 | A1* | 5/2016 | Lechot | A61B 17/1666 606/81 |

* cited by examiner

*Primary Examiner* — Andrew Yang
(74) *Attorney, Agent, or Firm* — DLA Piper LLP

(57) ABSTRACT

A system (200) and method (600) for identifying cutting tools for use during a surgical procedure are described. For example, the system includes a cutting tool assembly (210) including a shaft (212) having a cutting element (214) and at least one identifying feature (216) that uniquely corresponds to the cutting element. The system further includes a drive assembly (220) including a reference pin (224), a motor (230) mechanically connected to the drive assembly, a control unit (240) configured to activate the motor to move the cutting tool assembly such that the reference pin engages with the at least one identifying feature, a sensor system (226) configured to determine positioning information related to the reference pin when the reference pin engages the at least one identifying feature, and a computing unit (250) configured to receive the positioning information from the sensor system and identify the cutting element based upon the position information.

21 Claims, 7 Drawing Sheets

0
FEATURE-BASED SURGICAL TOOL IDENTIFICATION

CLAIM OF PRIORITY

This application is a continuation of U.S. patent application Ser. No. 16/521,796, filed Jul. 25, 2019, which is a continuation of U.S. patent application Ser. No. 16/473,974, filed Jun. 26, 2019, now U.S. Pat. No. 10,575,860, issued Mar. 3, 2020, which is a U.S. National Stage filing under 35 U.S.C. § 371 of International PCT Application No. PCT/US2018/015316, filed Jan. 25, 2018, which claims the benefit of priority to U.S. Provisional Application No. 62/450,458, titled "Feature-Based Surgical Tool Identification," filed Jan. 25, 2017, each of which is incorporated herein by reference in its entirety.

TECHNICAL FIELD

The present disclosure relates generally to identifying cutting tools for surgical procedures. More specifically, the present disclosure relates to identifying cutting tools using certain parameters to verify that the correct tools for a surgical procedure have been inserted into a drive assembly.

BACKGROUND

The use of computers, robotics, and imaging to aid orthopedic surgery is known in the art. There has been a great deal of study and development of computer-aided navigation and robotic systems used to guide surgical procedures. For example, surgical navigation systems can aid surgeons in locating patient anatomical structures, guiding surgical instruments, and implanting medical devices with a high degree of accuracy. Surgical navigation systems often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

Surgeons often utilize rotating cutting tools, such as drills and burs, with the aid of surgical navigation systems. It is important that the type of tool being used is consistent with the surgical plan to ensure that the system performs accurately and safely. For example, the use of an oversized bur diameter could produce an enlarged implant pocket, thereby resulting in improper or loose implant placement. Conversely, undersized burs can produce undersized implant pockets that require additional time to correctly size and/or shape. Similarly, the use of drill bits that are outside of the specifications for a particular procedure (e.g., maximum velocity, material, etc.) can be risky.

Tools are often labelled to avoid the above-described risks. However, the use of labels may not prevent confusion when multiple interchangeable tools are used during the same procedure. Labels can become damaged, covered with blood or other debris, or have other related issues. Furthermore, human error can occur even when labels are clearly discernible.

What is needed is an automatic tool detection system and method that allows the navigation system to identify the tool that has been inserted into the handpiece.

SUMMARY

There is provided a cutting tool identification system for use during a surgical procedure. The system includes a cutting tool assembly including a shaft having a cutting element and at least one identifying feature that uniquely corresponds to the cutting element. The system further includes a drive assembly comprising a reference pin, the drive assembly configured to receive at least a portion of the cutting tool assembly, a motor mechanically connected to the drive assembly, a control unit configured to activate the motor to move the cutting tool assembly such that the reference pin engages with the at least one identifying feature, a sensor system configured to determine positioning information related to the reference pin when the reference pin engages the at least one identifying feature, and a computing unit configured to receive the positioning information from the sensor system and identify the cutting element based upon the position information.

In some embodiments, the computing unit is further configured to determine whether the cutting element is suitable for use in a particular surgical procedure.

In some embodiments, the cutting element includes at least one of a drill bit and a cutting bur.

In some embodiments, the at least one identifying feature includes a plurality of detection components that extend axially from the cutting element at an intersection of the cutting element and the shaft.

In some embodiments, the at least one identifying feature includes a plurality of detection components equally spaced about a circumference of the shaft.

In some embodiments, the computing unit is further configured to identify the cutting element based upon the position information and at least one geometrical property of the at least one identifying feature.

In some embodiments, wherein the motor is configured to actuate the drive assembly rotationally. In some additional embodiments, the motor is further configured to actuate the drive assembly axially.

In some embodiments, the computing unit is further configured to detect contact between the reference pin and the at least one identifying feature.

In some embodiments, the reference pin includes a first conductive portion and the at least one identifying feature includes a second conductive portion. In some additional embodiments, the computing unit is further configured to detect contact between the reference pin and the at least one identifying feature by measuring a change in current resulting from the first conductive portion contacting the second conductive portion.

In some embodiments, the computing unit includes a database configured to store data correlating a plurality of cutting elements and associated identification information.

In some embodiments, the system further includes a display device operably connected to the computing unit. In some additional embodiments, the display device is configured to provide a notification to a user about a current state of the cutting tool assembly.

There is also provided a method for identifying cutting instruments for a surgical procedure. The method includes moving, by a motor, a drive assembly into contact with a cutting tool assembly, the cutting tool assembly including a cutting element including an identifying feature; detecting, by a computing device, contact of the drive assembly with the cutting tool assembly; collecting, by the computing device, cutting tool identification data relating to the cutting element; accessing, by the computing device, a database to compare the collected cutting tool identification data with data for known cutting tools to identify the cutting tool assembly; determining, by the computing device, whether the cutting tool assembly is approved for the surgical procedure; and notifying, by the computing device, a user of the results, wherein the notification is displayed on a display device operably connected to the computing device.

In some embodiments, collecting the cutting tool identification data relating to the cutting element includes rotating the cutting tool assembly within a drive assembly to a start position; retracting the cutting tool assembly within the drive assembly until the identifying feature abuts a reference pin attached to the drive assembly; collecting measurement parameters; extending the cutting tool assembly; rotating the cutting tool assembly a known amount; retracting the cutting tool assembly until the identifying feature abuts the reference pin again; and collecting additional measurement parameters. In some additional embodiments, the measurement parameters include axial contact position information and rotation angle information for the cutting element. In some additional embodiments, the measurement parameters further include an axial distance from an end of the cutting tool assembly to a surface of the identifying feature. In some additional embodiments, accessing the database to compare the collected cutting tool identification data with data for known cutting tools includes comparing the collected measurement parameters and the collected additional measurement parameters with data stored in the database to identify the cutting element.

In some embodiments, the cutting element includes at least one of a drill bit and a cutting bur.

In some embodiments, the identifying feature includes a plurality of detection components that extend axially from the cutting element.

In some embodiments, the identifying feature includes a plurality of detection components equally spaced about a circumference of a shaft attached to the cutting element.

The example embodiments as described above can provide various advantages over prior techniques. For example, the techniques as taught herein can reduce the chance that an improper cutting tool is used during a surgical procedure. The techniques also provide for more efficient surgical procedures as cutting mistakes resulting from improper cutting tools are avoided and time spent correcting the mistakes is eliminated.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
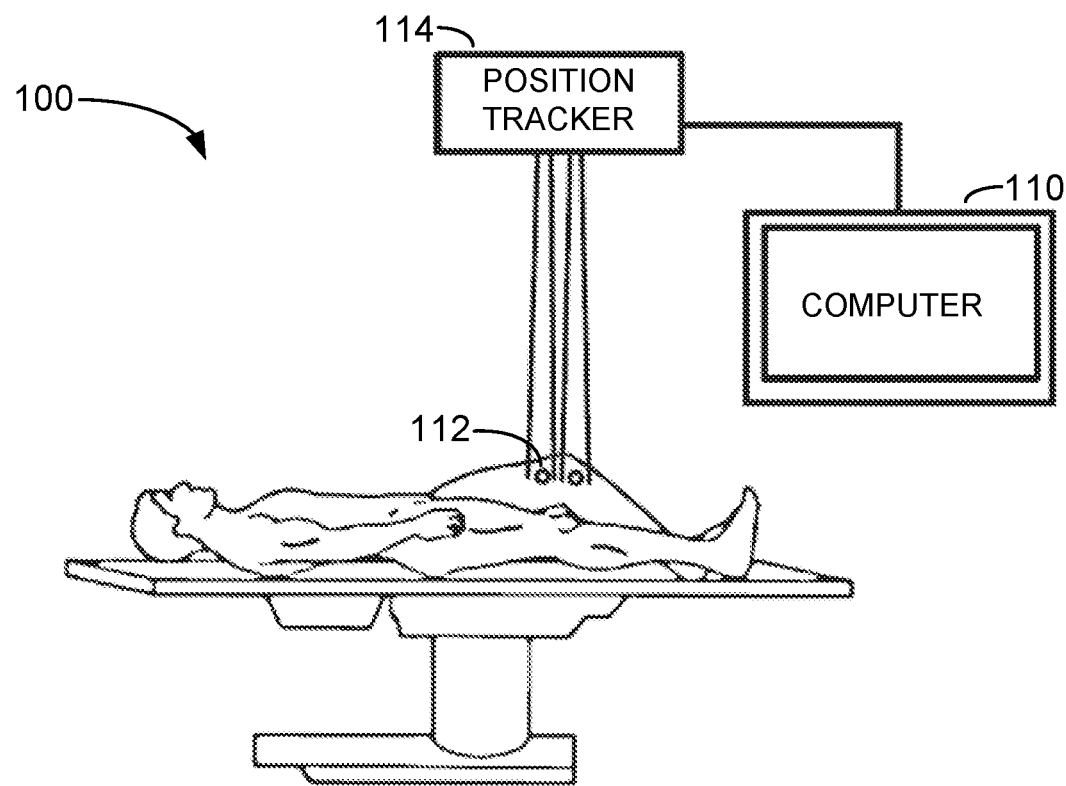
FIG. 1 depicts an illustration of an operating room with a system employing a surgical navigation system in accordance with certain embodiments of the invention.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

This disclosure describes example systems and methods of identifying and confirming that a selected cutting element is appropriate for use in a surgical procedure that was planned and will be performed with the aid of a surgical navigation system. In the following description, for purposes of explanation, numerous specific details are set forth in order to provide a thorough understanding of example embodiments. It will be evident to one skilled in the art, however, that embodiments can be practiced without these specific details.

For the purposes of this specification, the term "implant" refers to a prosthetic device or structure manufactured to replace or enhance a biological structure, either permanently or on a trial basis. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

The tool identification system as described herein is particularly adapted for surgical procedures that utilize surgical navigation systems, such as the NAVIO® surgical navigation system. Such procedures can include knee replacement revision surgery, as well as other surgical procedures. The disclosed tool identification system does not require extra sensors to be implemented to identify cutting tools because it can use the existing linear and rotary motion/sensing components of the NAVIO® hand-piece. NAVIO is a registered trademark of BLUE BELT TECHNOLOGIES, INC. of Pittsburgh, PA The tool identification system as described herein can be configured to utilize a wide variety of physical identification combinations or similar parameters to identify cutting tools, as compared to conventional systems that only employ magnetism or electrical current, such as Hall effect sensor techniques. Because the disclosed system can rely upon geometric features of a tool shaft, the system can be implemented through a simple machining operation, making the entire system more stable and less expensive when compared to conventional systems. In some implementations, no additional parts or components are necessary, which is an advantage over conventional systems that utilize magnets. The disclosed system also provides the ability to verify that the cutting tool is properly seated in a collet of a tool carriage.

The tool identification system as described herein can also allow a robotic system to identify and confirm tools that can be implemented with surgical navigation systems after the tools have been inserted into such systems. The tool identification system is robust with respect to tool identification and surgical environments, including environments that can be subjected to various cleaning and/or sterilization techniques.

FIG. 1 illustrates components of a surgical navigation system 100 that can be configured to implement the disclosed tool identification system according to various embodiments. The surgical navigation system 100 can assist a surgeon in performing certain surgical procedures that involve surgical implants, such as knee implants. In some implementations, the surgical navigation system 100 can also be used for procedures involving other joints such as hip replacement surgery.

In some examples, the surgical navigation system 100 can include a computer system 110 to provide a display for viewing location data provided by fiducials 112 as read by a position tracker 114. The fiducials 112 and position tracker 114 can provide data relevant to the precise location of any solid object to which they are firmly attached. For example, the fiducials 112 and position tracker 114 can allow the surgical navigation system 100 to track the bones in a patient's knee joint during a procedure. In certain implementations, the position tracker 114 can detect tracking spheres located on the fiducials 112 in order to gather location data for a patient for the femur and the tibia upon which a procedure is to be performed. In some examples, the fiducials 112 can be any suitable trackers, such as active trackers, passive trackers, optical trackers, or electromagnetic trackers. The position tracker 114 can be an infrared camera system, an electromagnetic field generator with a tracking system, or other similar tracking systems.

Figure 2:
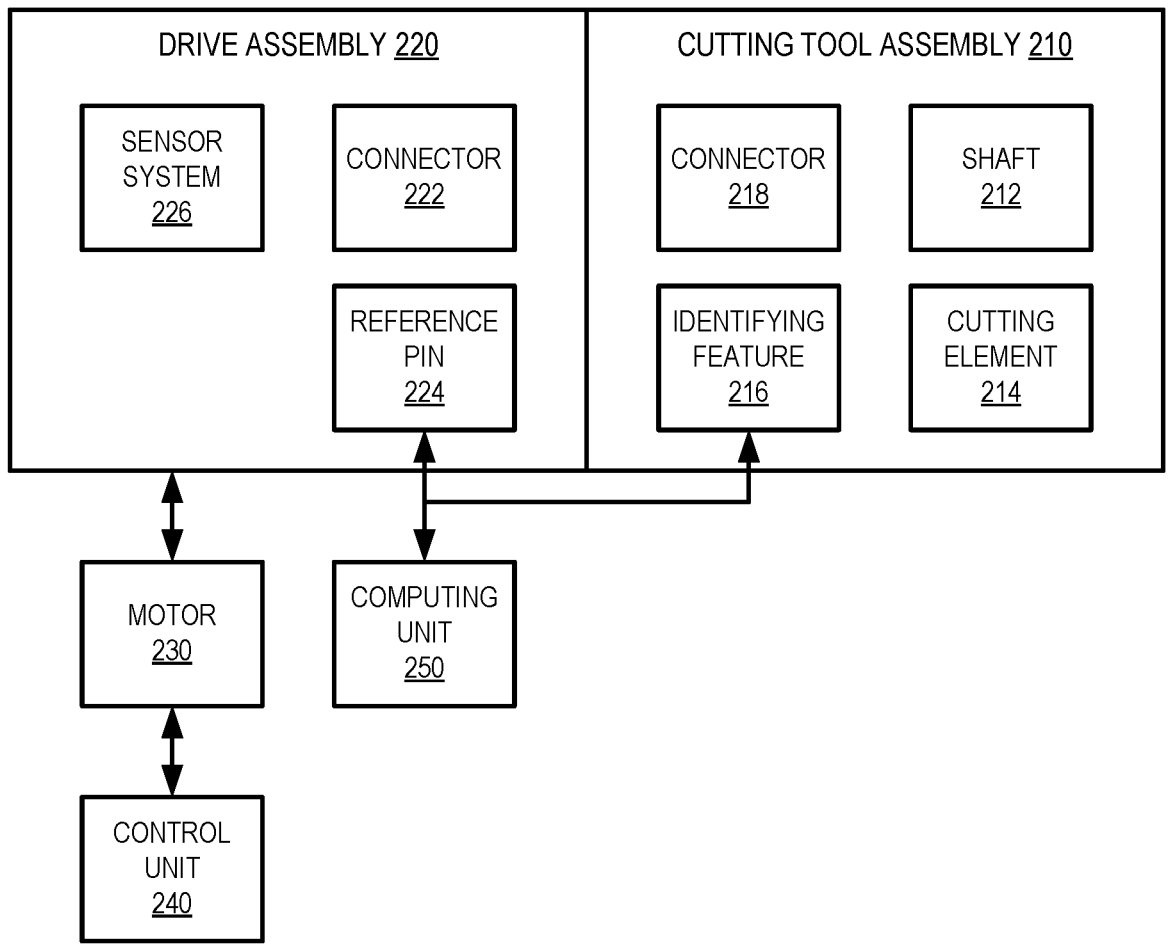
FIG. 2 depicts a block diagram depicting a system in accordance with an embodiment of the invention.

Referring to FIG. 2 with continuing reference to the foregoing FIG. 1, an electromechanical cutting tool identification system, generally designated as 200, is shown. The cutting tool identification system 200 can provide a reliable means to identify and verify cutting tools that can be implemented for use with a power tool system. The cutting tool identification system 200 can be used with surgical procedures, such as surgical procedures that involve implants, to verify that a particular cutting tool is consistent with the tool required for a particular surgical plan.

In certain implementations, the cutting tool identification system 200 can utilize relative elevations of geometric properties to identify a particular tool. The cutting tool identification system 200 can further rely on axial and rotational movement of the cutting tool assembly 210 to detect the geometric properties of a tool.

In some implementations, the cutting tool identification system 200 can include a cutting tool assembly 210, a drive assembly 220, a motor 230, a control unit 240, and a computing unit 250. The cutting tool assembly 210 can include a shaft 212 having a cutting element 214 and an identifying feature 216. The shaft 212 can be rotated and/or moved axially. The identifying feature 216 can uniquely correspond to the cutting element 214 and, in certain embodiments, can be coded to communicate the geometric properties of the cutting element 214. In certain other implementations, the identifying feature 216 can be configured to convey the material properties of the cutting element 214. In some examples, the cutting tool assembly 210 can also include a connector 218 for connecting the shaft to the drive assembly 220. The connector 218 can also be used to identify the location of an end of the shaft 212 to be used in measuring the elevations of one or more portions of the identifying feature 216.

In some examples, the cutting element 214 can be disposed on the shaft 212 either permanently or releasably and can be any suitable cutting tool, such as a drill bit or a cutting bur. In certain implementations, the identifying feature 216 can be a physical or mechanical structure(s) that is added to, or cut away from, the cutting tool assembly 210.

In certain embodiments, the drive assembly 220 can connect to the cutting tool assembly 210 at connector 218 with connector 222. The connection can be a conventional mechanical connection between the connectors 218 and 222 or the connection can be magnetic or friction-based. In some examples, the drive assembly 220 can extend or retract the cutting tool assembly 210 axially. In certain embodiments, the drive assembly 220 can also include a second motor to rotate the cutting tool assembly 210. The drive assembly 220 can include a reference pin 224 and a sensor system 226 for measuring the elevations of one or more portions of the identifying feature 216. In certain embodiments, the sensor system 226 can employ a wheel, an encoder, a pin, a Hall effect sensor, or any other known device for use in measuring the position of the cutting tool assembly 210.

In certain implementations, the motor 230 can be controlled by the control unit 240 to supply power to move the drive assembly 220, which moves the cutting tool assembly 210. The motor 230 can be separate from the drive assembly 220 as illustrated in FIG. 2 or can be implemented as a part of the drive assembly 220. In certain embodiments, the motor 230 can include two separate motors: a first motor for spinning the cutting tool assembly 210 and a second motor for axially moving the cutting tool assembly.

In certain embodiments, the cutting tool identification system 200 can employ the computing unit 250 to identify and verify the cutting element 214 when the cutting tool assembly 210 is inserted into the drive assembly 220. The cutting tool identification system 200 can identify the cutting element 214 based upon the identifying feature 216, which as noted above can include one or more simple physical components that can uniquely identify a particular cutting element 214. The uniqueness of the components can be defined by geometrical properties, such as component-to-component distance and component-to-component orientation.

In some examples, the identifying feature 216 can include a plurality of individual components. In various embodiments, the computing unit 250 can utilize the individual components to identify the cutting element 214 using a simple lookup table. In certain embodiments, the components can be measured relative to one another or relative to a constant distal location such as the end of the shaft 212.

The cutting tool identification system 200 can configure and implement the computing unit 250 to identify the cutting element 214 when the sensor system 226 characterizes the identifying feature 216. In some embodiments, the characterization can be a measurement of electrical, magnetic, or physical properties of the identifying feature.

In certain implementations, the computing unit 250 can be configured such that the cutting tool identification system 200 employs the reference pin 224 and sensor system 226 to characterize the identifying feature 216 when an abrupt change in a monitored electrical current occurs. In some embodiments, this characterization can occur when the reference pin 224 makes physical contact with the identifying feature 216 as the cutting tool assembly 210 is being retracted into the drive assembly 220. The retraction of the cutting tool assembly 210 can cause an abrupt rise in motor current, as detected by the sensor system 226, signifying a contact event within the computing unit 250. In other embodiments, the computing unit 250 can be used to characterize the identifying feature 216 when electrical contact between a reference pin 224 that has been electrically charged and the identifying feature 216 is detected.

In some embodiments, the sensor system 226 can be contained within a motor 230. For example, the sensor system 226 can be implemented as one or more Hall effect sensors that can measure the magnetic field orientation of different magnetic poles within the one or more motors 230. Magnetic field orientation changes with the operation of each such motor correlate to rotation of the cutting tool assembly 210, such as in 60 degree increments in the case of a 3-phase motor. In embodiments, magnetic field orientation changes can also be used to measure axial displacement of the cutting tool arrangement 210 such as where a lead screw is combined with a motor 230 to move the cutting tool arrangement axially. In such an example, the computing unit 250 can determine that the sensor system 226, in conjunction with the reference pin 224, has detected the relative heights of one or more components of the identifying feature 216.

In some embodiments, the drive assembly 220 can be configured to implement the sensor system 226 to encode the axial and rotational position of the shaft 212 as it characterizes the identifying feature 216. In certain implementations, the sensor system 226 can include two or more sensor systems (e.g., a first sensor system for rotation and a second sensor system for axial location) to characterize the identifying feature 216. In other embodiments, only one sensor system 226 may be implemented. In this example, the motor 230 can be used to rotate the bur a known amount without any feedback to verify it moved to an intended position as will be discussed in relation to FIGS. 4 and 5 as described below.

Figure 3:
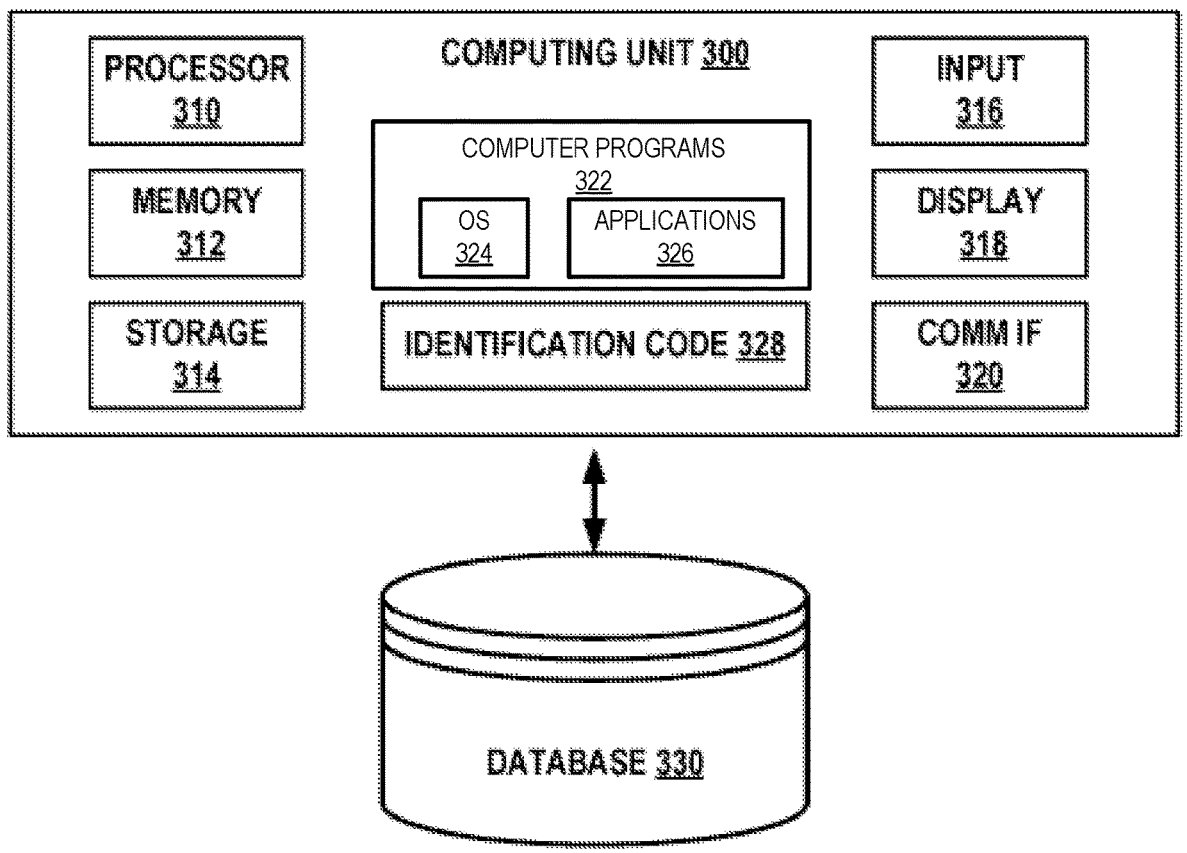
FIG. 3 depicts a block diagram depicting a system in accordance with an embodiment of the invention.

Referring to FIG. 3 with continuing reference to the foregoing figures, a computing unit, generally designated by numeral 300, that, for example, corresponds to the computing unit 250 shown in FIG. 2 is illustrated. The computing unit 300 can be configured to collect data, such as data indicative of relative linear and angular position data, from the control unit 240 and/or from the sensor system 226 shown in FIG. 2. The computing unit 300 can be implemented as a computer, computer system and/or a computing device. It is to be appreciated that embodiments of the computing unit 300 can be implemented by various types of operating environments, computer networks, platforms, frameworks, computer architectures, and/or computing systems.

Implementations of the computing unit 300 are described within the context of a device configured to perform various steps, methods, and/or functionality in accordance with embodiments of the described subject matter. It is to be appreciated that a computing device or computer system can be implemented by one or more computing devices. Implementations of computing unit 300 can be described in the context of "computer-executable instructions" that are executed to perform various steps, methods, and/or functionality in accordance with embodiments of the described subject matter.

In general, a computer system or computing device can include a combination of hardware and software. It can be appreciated that various types of computer-readable storage media can be part of a computer system or computing device. As used herein, the terms "computer-readable storage media" and "computer-readable storage medium" do not mean and unequivocally exclude a propagated signal, a modulated data signal, a carrier wave, or any other type of transitory computer-readable medium. In various implementations, a computer system or computing device can include a processor configured to execute computer-executable instructions and a computer-readable storage medium (e.g., memory and/or additional hardware storage) storing computer-executable instructions configured to perform various steps, methods, and/or functionality in accordance with embodiments of the described subject matter.

Computer-executable instructions can be embodied and/or implemented in various ways such as by a computer program (e.g., client program and/or server program), a software application (e.g., client application and/or server application), software code, application code, source code, executable files, executable components, routines, application programming interfaces (APIs), functions, methods, objects, properties, data structures, data types, and/or the like. Computing unit 300 can implement and utilize one or more program modules. Generally, program modules include routines, programs, objects, components, data structures, etc., that perform particular tasks.

Computing unit 300 can include a processor 310, memory 312, additional hardware storage 314, input devices 316, and display device 318. Computing unit 300 can contain one or more communication interfaces 320 that allow computing unit 300 to communicate with other computing devices and/or other computer systems. Communication interfaces 320 also can be used in the context of distributing computer-executable instructions.

Computing unit 300 can include and/or run one or more computer programs 322 implemented, for example, by software, firmware, hardware, logic, and/or circuitry of computing unit 300. Computer programs 322 can include an operating system 324 implemented, for example, by one or more exemplary operating systems described above and/or other type of operating system suitable for running on computing unit 300. Computer programs 322 can include one or more applications 326.

Computer programs 322 can implement computer-executable instructions that are stored in computer-readable storage media such as memory 312 or hardware storage 314, for example. Computer-executable instructions implemented by computer programs 322 also can be configured to provide one or more separate and/or stand-alone services.

The computing unit 300 can implement and perform various embodiments of the described subject matter. For example, computing unit 300 can utilize identification code 328 to identify the cutting element 214 shown in FIG. 2 using geometrical properties or other similar parameters. In certain embodiments, the identification code 328 can successfully identify the cutting element 214 and determine whether the cutting element is compatible with a particular surgical procedure. In other embodiments, the identification code 328 may not be able to identify the cutting element 214. The failure of the identification code 328 to identify the cutting element 214 can result when the cutting element has not been approved or used in the planning process for a given procedure.

The computing unit 300 can communicate to a user with the display device 318. The computing unit 300 can indicate when it has successfully identified the cutting element 214 on the display device 318. The computing unit 300 can indicate when the cutting element 214 is the proper tool for a surgical procedure on the display device 318. The computing unit 300 can indicate when the cutting element 214 cannot be identified with a warning on the display device 318. The computing unit 300 can indicate when the cutting element 214 is incompatible with a surgical procedure on the display device 318 with a similar warning.

The computing unit 300 can communicate with a database 330 that stores parameters for reference cutting tools and/or approved cutting tool designs. The parameters can include measured distances and measured orientations for reference cutting tools. The computing unit 300 can access the database 330 to compare linear and angular position data obtained from the sensor system 226 and/or the control unit 240 with information for reference cutting tools in the database 330. The information for reference cutting tools and/or approved cutting tool designs can represent measured distances and orientations that are unique for a particular cutting tool design.

Figure 4:
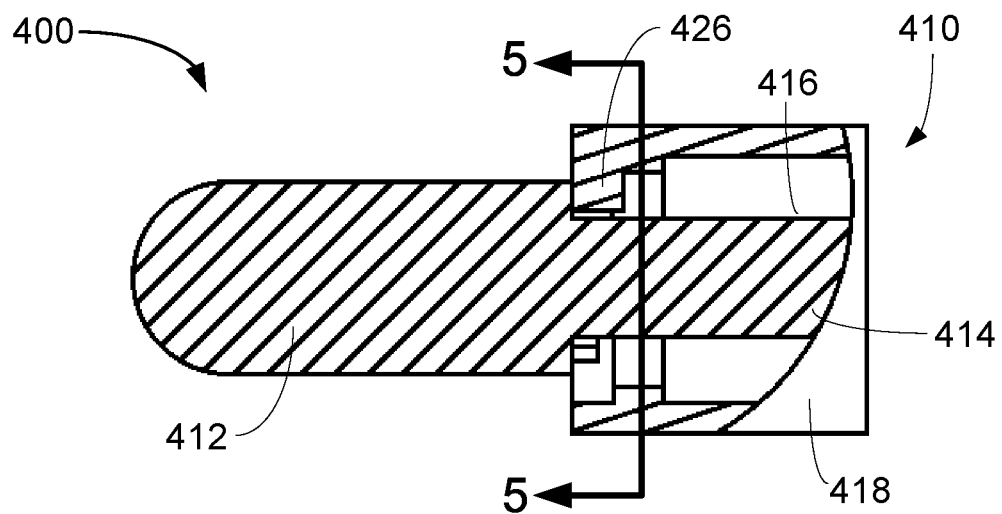
FIG. 4 depicts a cross section view in side elevation of a cutting tool assembly inserted into a drive assembly in accordance with an embodiment of the invention.
Figure 5:
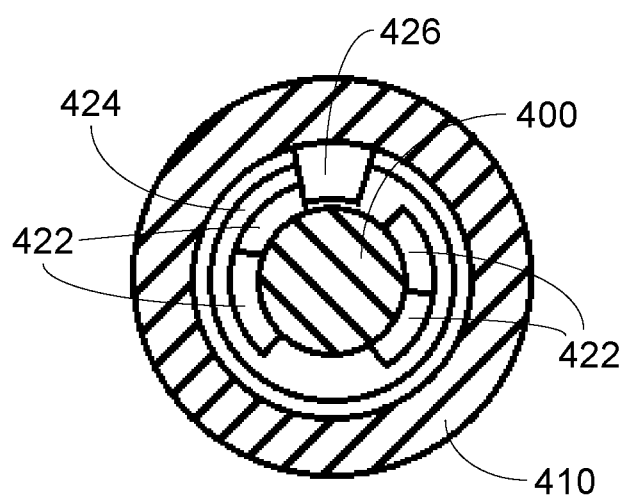
FIG. 5 depicts a cross-sectional view along line 5-5 of the cutting tool assembly inserted into the drive assembly shown in FIG. 4.

Referring to FIGS. 4 and 5, with continuing reference to the foregoing figures, a cutting tool assembly 400 can be inserted into a drive assembly 410. The cutting tool assembly 400 can be any suitable cutting tool assembly, such as the cutting tool assembly 210 depicted in FIG. 2 and described above. The drive assembly 410 can be any suitable drive assembly, such as the drive assembly 220 depicted in FIG. 2 and described above.

In certain implementations, the cutting tool assembly 400 can include a bur 412 and a substantially cylindrical shaft 414 that is sized and configured to fit into a receptacle 416 in the drive assembly 410 for mechanical connection thereof. The drive assembly 410 can include an essentially tubular cylindrical body 418 that forms the receptacle 416 for receiving the shaft 414.

As is further illustrated by FIGS. 4 and 5, the cutting tool assembly 400 can include a plurality of detection components 422 that extend axially away from the bur 412 where the bur meets the shaft 414. In certain embodiments, these detection components 422 collectively form an identifying feature 424, which can be the same as the identifying feature 216 illustrated in FIG. 2 and described above. The drive assembly 410 can include a reference pin 426 for assisting with the detection of the identifying feature 424.

In certain embodiments, the identifying feature 424 can be repeated around the circumference of the shaft 414. In some examples, the identifying feature 424 can be repeated in 60° increments around the circumference of the shaft 414. In other examples, the identifying feature 424 can be repeated in 120° or 180° increments. Preferably, the identifying features 424 can be arranged in a symmetrical arrangement to avoid rotational imbalance when the cutting tool assembly 400 is used in a surgical procedure. The reference pin 426 can be used to sample the relative height of the detection components 422 at various points around the shaft 414. Alternatively, the reference pin 426 can be used to measure the distance from an end of the shaft 414 to each detection component 422 as the cutting tool assembly 400 is rotated during an identification procedure. In some examples, only a portion of the identifying feature 424 can be sensed during an identification procedure.

In certain embodiments of operation, the drive assembly 410 can axially extend the cutting tool assembly 400 to a "start" position where the reference pin 426 is far enough removed from the identifying feature 424 that the cutting tool assembly 400 can rotate freely. In certain implementations, the motor 230 can be configured to engage a lead screw that axially extends or retracts the cutting tool assembly 400 into or out of the drive assembly 410. In some examples, the computing unit 300 can use the sensor system 226 to keep track of the amount of axial extension of the cutting tool assembly 400 as compared to a reference point. The drive assembly 410 can then retract the shaft 414 until the reference pin 426 contacts a detection component 422 of the identifying feature 424. The computing unit 250, shown in FIG. 2 and described above, can record the axial contact position and the rotation angle relative to the start or "zero" position. The shaft 414 can be extended axially, rotated, and retracted until the reference pin 426 contacts the next detection component 422 that makes up the identifying feature 424.

In certain implementations, the start or "zero" position can be removed from the above-described steps by repeating the steps "n" times with a prescribed rotation increment being applied during each cycle. The increments can be measured in degrees (e.g., n=360/angular increment). Because the identifying feature 424 repeats, the cutting element 420 can then be identified by matching the measured data with catalogue data using the computing unit 250, shown in FIG. 2.

With reference again to FIGS. 4 and 5, the identifying feature 424 can include detection components 422 arranged around the shaft 414 in 60 degree increments. In certain embodiments, this arrangement can be compatible with a three phase motor 230, which has a resolution of 120 degrees between each pole pair so that all three detection components 422 can be detected by energizing each pole pair in turn and retracting the shaft until the detection component 422 hits the reference pin 426. In this manner, the motor 230 can be used to rotate the cutting tool assembly 210 a known amount without the need for a rotational sensor while characterizing the entire identifying feature 424. Further, because the starting rotational position may be unknown relative to the pattern in the identifying feature 424, the identification process described has some redundancy that can ensure that all of the detection components 422 will be read.

Figure 6:
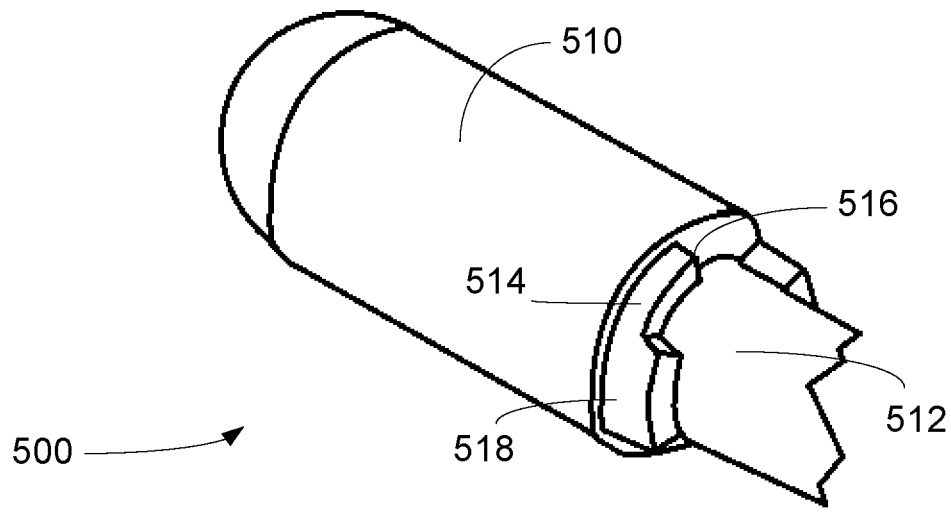
FIG. 6 depicts a fragmentary perspective view of a cutting tool assembly highlighting an example of an identifying feature in accordance with an embodiment of the invention.
Figure 7:
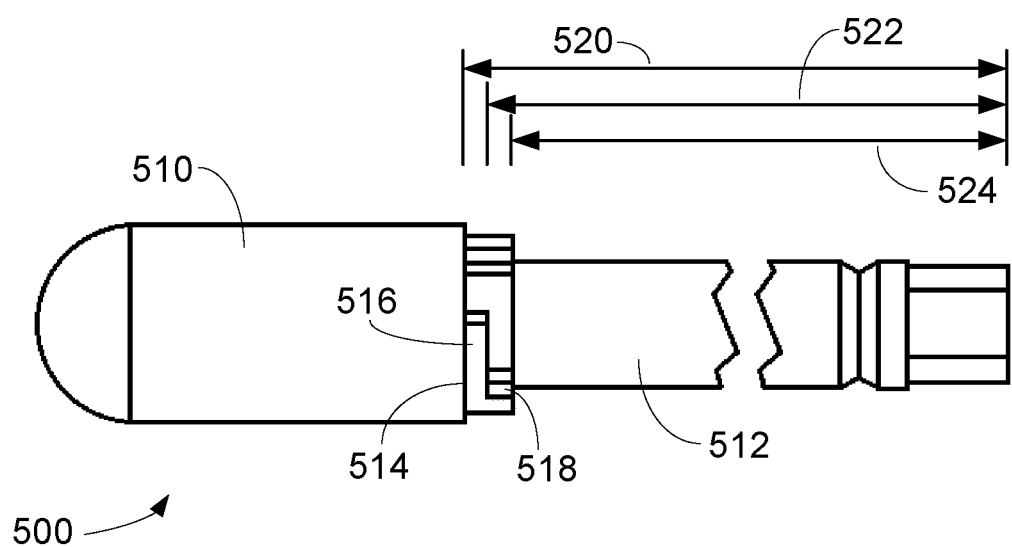
FIG. 7 depicts an alternative fragmentary perspective view of the cutting tool assembly shown in FIG. 6.

Referring to FIGS. 6 and 7, with continuing reference to the foregoing figures, a cutting tool assembly, generally designated by the numeral 500, is shown. The cutting tool assembly 500 can be any suitable cutting tool assembly, such as the cutting tool assembly 210 shown in FIG. 2 or cutting tool assembly 400 shown in FIGS. 4 and 5.

In certain embodiments, the cutting tool assembly 500 has a bur head 510, a bur shaft 512, and an identifying feature 514. The identifying feature 514 can be formed from a plurality of partial annular rings 516, 518. In this exemplary embodiment, the partial annular rings 516, 518 can include predetermined axial dimensions so that the distances 520, 522, and 524 are fixed to form a set of predetermined geometric properties for a particular cutting tool assembly 500.

The geometric properties can be preselected so that a particular set of geometric properties can be correlated with the bur head 510. As a result, the computing unit 300 shown in FIG. 3 can utilize the distances 520, 522, and 524 with a set of geometric properties for a known rotating tool or cutting tool in database 330 to identify the cutting tool assembly 500.

In this exemplary embodiment, only the distances 520, 522, and 524 are used to identify the bur head 510. It should be understood that the number of unique tools that can be encoded with this technique is limited only by the resolution with which axial island positions such as detection components 422 or partial annular rings 516, 518 can be detected, which is a combination of axial resolution, sensor quality, and manufacturing tolerances.

Figure 8:
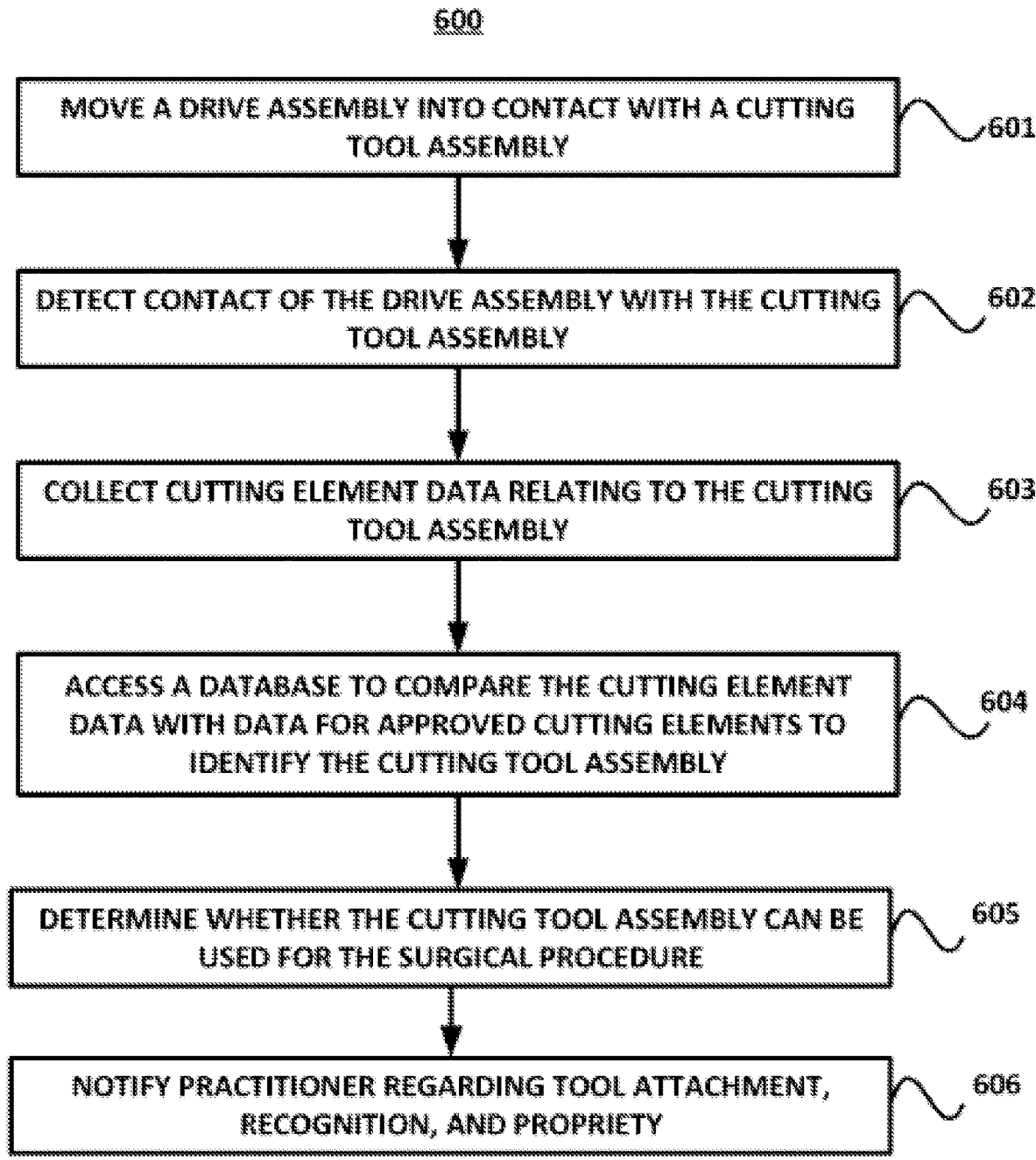
FIG. 8 depicts a block diagram depicting a method in accordance with an embodiment of the invention.

Referring to FIG. 8 with continuing reference to the foregoing figures, an exemplary method 600 is illustrated as an embodiment of an exemplary cutting element identification process in accordance with certain embodiments of the described subject matter. The method 600, or portions thereof, can be performed by or with the aid of one or more computing devices, a computer system, computer-executable instructions, software, hardware, firmware or a combination thereof in various embodiments. For example, method 600 can be performed by surgical navigation system 100 or other suitable systems.

As shown in FIG. 8, a drive assembly can be moved 601 into contact with a cutting tool assembly. In certain embodiments, the drive assembly can be the drive assembly 220 shown in FIG. 2 or the drive assembly 410 shown in FIGS. 4 and 5. The cutting tool assembly can be the cutting tool assembly 210 shown in FIG. 2, the cutting tool assembly 400 shown in FIGS. 4 and 5, or the cutting tool assembly 500 shown in FIGS. 6 and 7. Other cutting tool assemblies and drive assemblies will be apparent to those of skill in the art.

A computing device can detect 602 contact of the drive assembly with the cutting tool assembly. In this exemplary embodiment, the contact can be detected by the computing unit 250 shown in FIG. 2 or the computing unit 300 shown in FIG. 3. In some exemplary embodiments, the detection occurs when the identifying feature 216 is detected by the sensor system 226 shown in FIG. 2 or when the identifying feature 424 contacts the reference pin 426 shown in FIGS. 4 and 5.

The computing device can further collect 603 cutting element data relating to the cutting tool assembly 400. In certain embodiments, the cutting element data can be collected by having the drive assembly 220 rotate the shaft 414 shown in FIGS. 4 and 5 with the reference pin 426 repeatedly engaging with the detection features 422, as described herein, to characterize the identification feature 424. The resultant data is collected by, for example, the computing unit 250 shown in FIG. 2 or the computing unit 300 shown in FIG. 3 and stored in memory such as memory 312 as shown in FIG. 3.

The computing device can access 604 a database to compare the cutting element data collected by the reference sensor 426 with data for approved cutting elements, according to a surgical plan, to identify the cutting tool assembly 400. In this exemplary embodiment, the database can be the database 330 shown in FIG. 3.

A cutting element identification system can determine 605 whether the cutting tool assembly 400 can be used for the surgical procedure. In this exemplary embodiment, the cutting element identification system can be the cutting element identification system 200 shown in FIG. 2.

The computing system can notify 606 a practitioner via a graphical user interface regarding the determination 605 whether the cutting tool assembly 400 can be used for the surgical procedure. In certain embodiments, these notifications can include a message that the cutting tool assembly is properly attached, that it has been recognized by the system and whether or not it complies with the surgical plan. In the event that it is determined 605 that an improper cutting element has been detected, an error message can also be conveyed to the user through the use of lights, sounds, displays or a combination thereof. The system could also be disabled until an appropriate cutting tool assembly is inserted.

Figure 9:
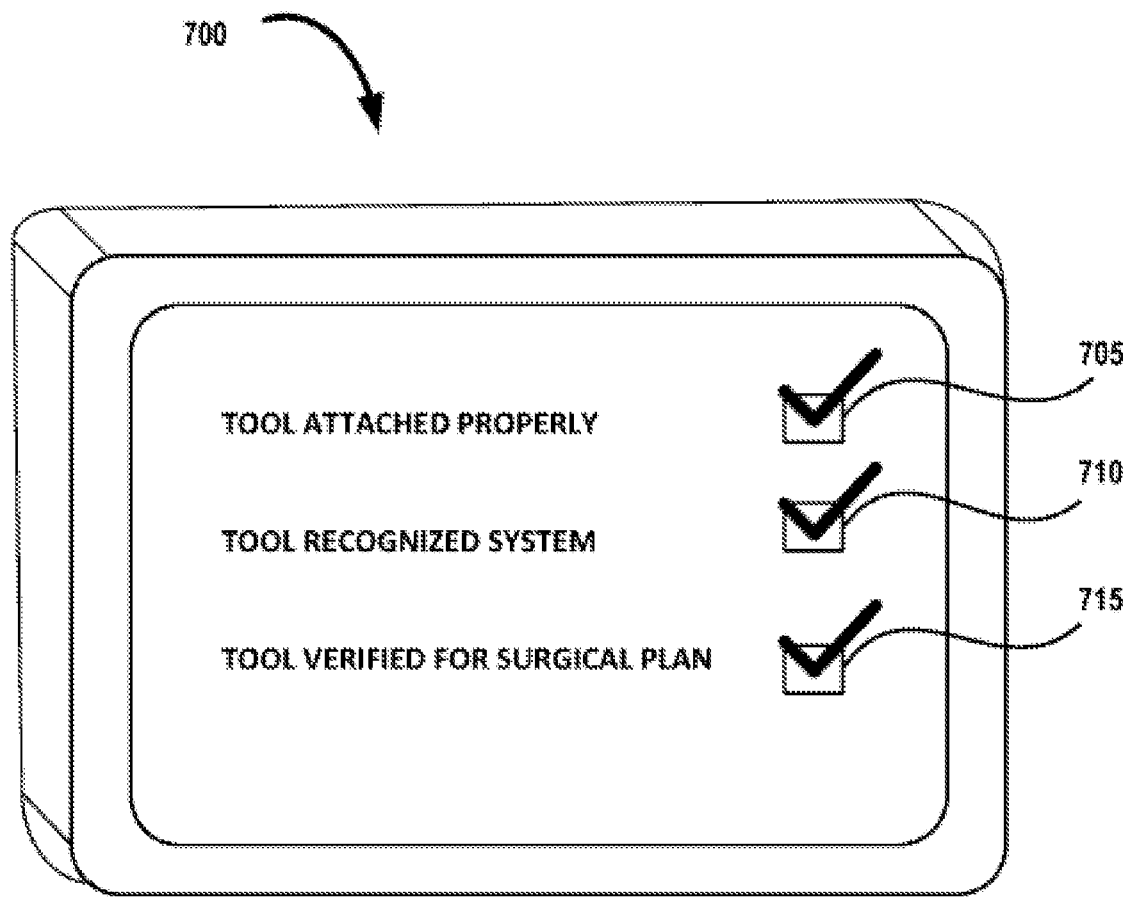
FIG. 9 depicts an illustration of a graphical user interface providing a message to a user in accordance with an embodiment of the invention.

In certain embodiments, such as is illustrated in FIG. 9, a display device 700 can be configured to communicate to a user such as the practitioner described above that a cutting tool assembly is attached properly 705, whether or not the cutting tool is recognized by the system 710, and whether or not the cutting tool will work for the identified surgical plan 715.

An advantage of certain embodiments of the disclosed cutting element identification system 200 is that the tool identification relies upon geometric, physical features on a shaft 414 of a cutting tool assembly 400. The identifying features 424 can be provided through simple machining operations without the need to incorporate additional parts or technical complexity into the cutting tool assembly 400. Moreover, the cutting tool identification system 200 can verify that a cutting tool assembly 400 is properly seated in the drive assembly and verify the axial location of the tool due to the fact that the drive assembly will not be able to put the reference pin in contact with the identification feature if the cutting tool assembly is improperly seated in the drive assembly.

It should be noted that, as described herein, some implementation of the tool identification system can use both rotational and axial position information to encode rotating tool, cutting tool, and/or bur identification information through the use of unique patterns. Such embodiments may have higher rotary resolutions, which can be obtained through the use of Hall effect sensors or a rotary encoder.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for tool identification during a surgical procedure, the system comprising:
   one or more tool assemblies, each tool assembly comprising a shaft, a tool tip joined to the shaft, and one or more identifying features disposed on the shaft proximally of the tool tip, wherein the one or more identifying features correspond to the tool tip;
   a drive assembly configured to selectively couple to each tool assembly to form a drive-tool assembly;
   one or more processors; and
   a non-transitory, computer-readable medium storing instructions that, when executed, cause the system to:
      actuate the drive-tool assembly to engage the drive assembly with the one or more identifying features;
      receive position information associated with the drive assembly when engaged with the one or more identifying features; and identify the tool assembly of the drive-tool assembly from amongst the one or more tool assemblies based on the position information.

2. The system of claim 1, wherein the one or more identifying features comprise one or more protrusions extending axially from the shaft.

3. The system of claim 2, wherein the one or more protrusions comprise a plurality of protrusions spaced about a circumference of the shaft.

4. The system of claim 3, wherein the plurality of protrusions are arranged symmetrically about the circumference of the shaft.

5. The system of claim 1, wherein the one or more identifying features comprise one or more partial annular rings arranged about the circumference of the shaft.

6. The system of claim 1, wherein each of the one or more identifying features comprises a conductive portion configured, in the drive-tool assembly, to contact a conductive feature of the drive assembly.

7. The system of claim 6, wherein the instructions, when executed, further cause the system to:
measure a current related to the conductive feature; and
detect coupling of the tool assembly to the drive assembly based on a change in the measured current caused by contact between the conductive portion and the conductive feature.

8. The system of claim 1, wherein the drive assembly further comprises a reference feature, and
wherein the instructions that cause the system to actuate the drive-tool assembly comprise instructions that, when executed, cause the system to move the reference feature to contact the one or more identifying features.

9. The system of claim 8, wherein the position information is related to a position of the reference feature when in contact with the one or more identifying features.

10. The system of claim 9, wherein the position information comprises one or more of an axial position of the reference feature and a rotational position of the reference feature when in contact with each of the one or more identifying features.

11. The system of claim 1, wherein the instructions that cause system to identify the tool assembly of the drive-tool assembly from amongst the one or more tool assemblies comprise instructions that, when executed, cause the system to:
compare the position information with tool identification data from a database; and
identify the tool assembly of the drive-tool assembly based on the comparison.

12. The system of claim 1, wherein the instructions, when executed, further cause the system to:
determine whether the identified tool assembly is approved for the surgical procedure based on a surgical plan; and
notify a user of the determination.

13. The system of claim 12, further comprising a display device,
wherein the instructions that cause the system to notify a user of the determination comprise instructions that, when executed, cause the system to display the determination on the display device.

14. The system of claim 1, wherein each tool tip comprises a cutting element selected from the group consisting of a drill bit and a cutting burr.

15. A system for tool identification during a surgical procedure, the system comprising:

a tool database storing tool identification profiles for a plurality of tool assemblies, wherein each of the plurality of tool assemblies in the tool database comprises a tool tip and one or more identifying features corresponding to the tool tip;
one or more processors;
a non-transitory, computer-readable medium storing instructions that, when executed, cause the system to:
detect coupling of a tool assembly with a drive assembly,
collect, via one or more sensors of the drive assembly, tool identification data related to the one or more identifying features of the tool assembly, and
compare the tool identification data to one or more of the tool identification profiles in the tool database to identify the tool assembly from the plurality of tool assemblies.

16. The system of claim 15, wherein the instructions, when executed, further cause the system to:
determine whether the tool assembly is approved for the surgical procedure based on a surgical plan; and
notify a user of the determination.

17. The system of claim 16, further comprising a display device,
wherein the instructions that cause the system to notify a user of the determination comprise instructions that, when executed, cause the system to display the determination on the display device.

18. The system of claim 15, further comprising the drive assembly, wherein the drive assembly comprises a reference pin configured to engage the one or more identifying features of the tool tip.

19. The system of claim 18, where the instructions that cause the system to collect tool identification data comprise instructions that, when executed, cause the system to:
cause the tool assembly to move with respect to the drive assembly to contact the one or more identifying features with the reference pin; and
collect, via the one or more sensors, one or more sets of measurement data associated with the contact between the one or more identifying features and the reference pin.

20. The system of claim 19, wherein each set of measurement data comprises axial position information and rotational position information associated with the contact between the one or more identifying features and the reference pin.

21. A system for tool identification during a surgical procedure, the system comprising:
one or more tool assemblies, each tool assembly comprising a shaft, a tool tip joined to the shaft, and one or more identifying features disposed on the shaft proximally of the tool tip, wherein the one or more identifying features correspond to the tool tip;
a drive assembly configured to selectively couple to each tool assembly to form a drive-tool assembly;
one or more processors programmed to cause the system to:
actuate the drive-tool assembly to engage the drive assembly with the one or more identifying features;
receive position information associated with the drive assembly when engaged with the one or more identifying features; and
identify the tool assembly of the drive-tool assembly from amongst the one or more tool assemblies based on the position information.

* * * * *